US011426606B2

(12) United States Patent
Traneus (10) Patent No.: US 11,426,606 B2
(45) Date of Patent: Aug. 30, 2022

(54) METHOD AND SYSTEM OF EVALUATING A RADIATION THERAPY TREATMENT PLAN

(71) Applicant: RaySearch Laboratories AB, Stockholm (SE)

(72) Inventor: Erik Traneus, Uppsala (SE)

(73) Assignee: RAYSEARCH LABORATORIES AB, Stockholm (SE)

( * ) Notice: Subject to any disclaimer, the term of this patent is extended or adjusted under 35 U.S.C. 154(b) by 0 days.

(21) Appl. No.: 17/424,195

(22) PCT Filed: Jan. 29, 2020

(86) PCT No.: PCT/IB2020/050672
§ 371 (c)(1),
(2) Date: Jul. 20, 2021

(87) PCT Pub. No.: WO2020/152660
PCT Pub. Date: Jul. 30, 2020

(65) Prior Publication Data
US 2022/0040501 A1    Feb. 10, 2022

(30) Foreign Application Priority Data
Jan. 21, 2019    (EP) .................................... 19152863

(51) Int. Cl.
*A61N 5/10*    (2006.01)
(52) U.S. Cl.
CPC ......... *A61N 5/1064* (2013.01); *A61N 5/1031* (2013.01)
(58) Field of Classification Search
CPC .................. A61N 5/103; A61N 5/1031; A61N 5/1037–1039; A61N 5/1048;
(Continued)

(56) References Cited

U.S. PATENT DOCUMENTS 8,829,476 B2 * 9/2014 Keppel .................. A61N 5/103
250/492.3

FOREIGN PATENT DOCUMENTS

CN    106163612 A    11/2016
CN    110475588 A    11/2019
(Continued)

OTHER PUBLICATIONS

Grassberger et al. "Variations in Linear Energy Transfer within Clinical Proton Therapy Fields and the Potential for Biological Treatment Planning." Int. J. Radiation Oncology Biol. Phys., vol. 80, No. 5, 2011, pp. 1559-1566, https://www.sciencedirect.com/science/article/pii/S036030 Accessed Dec. 1, 2021 (Year: 2011).*
(Continued)

*Primary Examiner* — Carrie R Dorna
(74) *Attorney, Agent, or Firm* — Faegre Drinker Biddle & Reath LLP (57) ABSTRACT

A method of evaluating a radiation therapy (RT) treatment plan for a treatment volume, divided into sub-volumes and having a target volume and one or more organs at risk, OAR. It includes obtaining a RT treatment plan; calculating the linear energy transfer, LET, in each sub-volume; dividing the dose distribution into doses of a first category and a second category in each sub-volume, wherein the first category comprises doses with energy depositions with an LET below a first LET threshold and the second category comprises doses with energy depositions with an LET above a second LET threshold; determining amounts of doses of the first and of the second category in each sub-volume; and performing an analysis of the quality of the RT treatment plan by metrics based on the obtained distribution of doses of the first and of the second category in the target volume and in the OAR.

15 Claims, 4 Drawing Sheets

(58) Field of Classification Search
CPC .. A61N 5/1064; A61N 5/1065; A61N 5/1067; A61N 5/107; A61N 5/1071; A61N 2005/1087
See application file for complete search history.

(56) References Cited

FOREIGN PATENT DOCUMENTS

| | | |
|---|---|---|
| EP | 2 848 284 A1 | 3/2015 |
| WO | WO-2007/126782 A2 | 11/2007 |

OTHER PUBLICATIONS

Niemantsverdriet, Maarten, et al., "High and Low LET Radiation Differentially Induce Normal Tissue Damage Signals," International Journal of Radiation: Oncology Biology Physics, vol. 83, No. 4, 2012, pp. 1291-1297.

\* cited by examiner

METHOD AND SYSTEM OF EVALUATING A RADIATION THERAPY TREATMENT PLAN

This application is the National Stage of International Application No. PCT/IB2020/050672, filed Jan. 29, 2020, and claims benefit of European Patent Application No. 19152863.7, filed Jan. 21, 2019, the entire contents of which are incorporated by reference herein.

FIELD OF THE INVENTION

The present disclosure relates in general to the field of radiation therapy treatment, in particular the generation, optimization and evaluation of a radiation therapy treatment plan.

BACKGROUND OF THE INVENTION

Cancer is a wide spread disease that expresses itself through the errant growth of abnormal cells. If the uncontrolled growth of these cells is not stopped, it can be fatal. The fatal trend of cancer worldwide is steadily increasing along with the overall estimated cost for cancer management. This has led to an increased demand from the public to develop more effective tools and technologies for treating and curing the disease. With the rapid advancement of medical imaging, tumors are being diagnosed in early stages when they still are local or regional. Different kinds of radiation therapy, brachytherapy, particle therapy and chemotherapy are effective in treating local cancer cells, or tumors.

Radiation therapy is a modality of cancer treatment that uses ionizing radiation that damages the DNA and causes cell death within the region being irradiated. Hence, the goal of radiation therapy is to deliver a radiation dose high enough to kill all the target tumor cells while simultaneously minimizing the damage to surrounding healthy structures. The unit of measure derived from the SI system is the Gray (Gy), which is defined as one Joule of energy absorbed per kilogram of matter.

Radiation therapy can use e.g. high energy photons (X-rays) or beams of protons or heavier ions like helium or carbon. For simplicity, from here on, we will refer to protons while all said about protons in this context also applies to other ions like helium or carbon. Different types of radiation have different cell kill capacity. For photons the cell damage is proportional to the absorbed energy (=dose). For protons the cell damage in addition depends on the ionization density per proton along the proton track. The ionization density depends on the energy of the proton. The ionization density is quantified in terms of linear energy transfer or LET i.e. energy loss per distance (common unit is MeV/cm or KeV/μm). The LET is low at high proton energy. The LET increases towards lower proton energy, reaches a maximum and then decreases. The LET maximum is reached when the residual range of the proton is small and hence occurs in the Bragg peak.

Since there is a need to kill the tumor cells as effectively as possible, high dose and LET are desirable inside the tumor. In healthy tissue outside of the tumor it desirable to have as low dose and low LET as possible.

The quality of a radiotherapy plan is usually judged by its dose conformity, treatment delivery time and radiobiological effectiveness. The dose conformity describes how well the high radiation dose region conforms to the target tumor and spares the surrounding healthy tissue, while treatment delivery time describes how long a treatment takes and the efficiency of the treatment machines used. As discussed above, an additional factor that may affect the effectiveness of treatment is the linear energy transfer (LET) distribution. A high LET is associated with increased cell damage that is being done to both tumor cells, as well as surrounding cells.

Modern radiation therapy treatment planning typically involves the following set of steps: patient imaging, target volume definition (i.e., structure contouring), dose prescription, machine and particle type selection, parameter definition, beam configuration optimization, plan generation, plan optimization and quality assurance and/or quality control.

In the field of radiation therapy treatment planning, treatment planners can generate different types of radiation therapy treatment plans for external radiation treatment. In order to generate a treatment plan, the specialist needs to identify the region to be treated in the patient's body and assess organs-at-risk (OAR) using conventional scanning techniques like computer tomography (CT). The target volume is usually an organ in a patient's body that is affected by a tumor, for example a prostate. However, studies have shown that the quality of a treatment plan is linked to the experience of the person performing the treatment, quality of the imaging devices and treatment devices, as well as many technical parameters like beam quality. This suggests that many treatment plans have room for improvement, especially if the treatment plan was prepared by less experienced personnel. Moreover, the use of inadequate planning methods, early termination of the optimization process, or measuring plan quality in an inadequate way can be a significant detriment to treatment quality.

Once the regions to be treated are imaged, physicians contour the tumor and OAR as well as prescribe the desired dose to treat the tumor. Thereafter, medical physicists start to work on the plan generation and generate the plan with one or multiple fields for treating the patient. A large number of human work hours are being spent on plan optimization and quality control to minimize the detrimental effects to the surrounding tissues and increase the plan effectiveness. This suggests additional expenses to the hospital, the society and creates challenges of delivering radiation treatment on time.

As mentioned above, one of the parameters that may contribute to the radiation treatment effectiveness is the distribution of LET in the target volume and in the surrounding tissues. It is well established that high LET radiation results in lower cell survival per absorbed dose than low LET radiation.

With increasing LET, the damage becomes more severe and more difficult to repair resulting in higher radiation lethality which is reflected by a higher relative biological effectiveness (RBE). As an example, the publication "High and Low LET Radiation Differentially Induce Normal Tissue Damage Signals" from M. Niemantsverdriet, M. Goethem, R. Bron, W. Hogewerf, S Brandeburg, J. Langendijk, P. Luijk, R. Coppes, *International Journal of Radiation Oncology and Biology Physics*, Volume 83, Issue 4, 15 Jul. 2012, Pages 1291-1297 presents a discussion of the biological effects when the LET is too low and when the LET is high enough. This confirms that LET optimization is a significant problem that has not yet been solved in practice. Thus, there is a need to generate an effective treatment plan and prevent secondary mutagenic effects.

Despite all of the research that has been conducted in the field in order to account for LET variations through optimization, there is still a need to further improve LET optimization in such a way that it comes to practical use and can improve radiation therapy treatment plan effectiveness.

SUMMARY OF THE INVENTION

It is an object of the present invention to provide methods to evaluate radiation therapy treatment plan quality. The evaluation may be visualized and/or used to generate a new radiation therapy treatment plan by a radiation therapy treatment planning system or machine, or to adjust/improve existing radiation therapy treatment plans generated by a treatment planning system or machine.

According to one aspect there is provided a method for generating a radiation therapy treatment plan used in a radiation therapy apparatus for a treatment volume of a body having a target volume and one or more organs at risk, OAR. The treatment volume comprises a plurality of sub-volumes. The method comprises the steps of:

obtaining a radiation therapy treatment plan for the treatment volume, the radiation therapy treatment plan comprising a dose distribution for radiation treatment with the radiation therapy apparatus for the treatment volume of the body having the target volume and the OAR;

calculating the linear energy transfer, LET, in each sub-volume based on the dose distribution to obtain an LET distribution over the treatment volume;

dividing the dose distribution into doses of a first category and a second category in each sub-volume, wherein the first category comprises doses with energy depositions with an LET below a first LET threshold and the second category comprises doses with energy depositions with an LET above a second LET threshold;

determining amounts of doses of the first and of the second category in each sub-volume to obtain a distribution of doses of the first and of the second category over the treatment volume; and performing an analysis of the quality of the radiation therapy treatment plan by metrics based on the obtained distribution of doses of the first and of the second category in the target volume and in the OAR.

In one embodiment the amount of dose of the second category in each sub-volume is specified in absolute numbers as absorbed dose and in another embodiment the amount of dose of the second category in each sub-volume is specified as a fraction of the amount of dose of the second category in relation to the total dose per sub-volume.

In a preferred embodiment, the first and second LET thresholds are the same. In an alternative embodiment, the first and second LET thresholds are different.

In an advantageous embodiment, one or more additional LET thresholds may be used to subdivide the doses of the first and/or of the second category into subcategories comprising doses with energy depositions with an LET below or above the one or more additional LET thresholds.

In yet another embodiment the first LET threshold and the second LET threshold are selectable by a user of the radiation therapy apparatus and/or treatment planning system.

In a preferred embodiment, the method further comprises visualizing the obtained distribution of doses of the first and of the second category over the treatment volume, such that regions with excessive concentrations of doses of the first and of the second category are assessable.

In another embodiment, the step of visualizing comprises visualizing the total dose and LET distributions together with the obtained distribution of doses of the first and of the second category over the treatment volume, wherein the amount of dose of the second category in each sub-volume is specified as a fraction of the amount of dose of the second category in relation to the total dose per sub-volume, such that regions with combined excess of high LET concentration and excessive concentration of first or second dose category are assessable.

In an advantageous embodiment, the step of obtaining a radiation therapy treatment plan comprises obtaining an initial, estimated radiation therapy treatment plan (e.g. based on standard generic models), the method further comprising:

generating a new radiation therapy treatment plan for the treatment volume by performing a parameter optimization for a set of parameters of the radiation therapy apparatus with a computer using the amount of doses of the second category in each sub-volume, such that the amount of dose of the second category is below a first threshold in the OAR, and above a second threshold in the target volume.

In an alternative embodiment, the step of obtaining a radiation therapy treatment plan comprises obtaining an existing radiation therapy treatment plan for the treatment volume, the method further comprising:

adjusting the existing radiation therapy treatment plan for the treatment volume by performing a parameter optimization for a set of parameters of the radiation therapy apparatus with a computer using the amount of doses of the second category in each sub-volume, such that the amount of dose of the second category is below a first threshold in the OAR, and above a second threshold in the target volume, while at least preserving the plan quality of the existing radiation therapy treatment plan, thereby generating an improved radiation therapy treatment plan.

In a further preferred embodiment, the parameter optimization may include at least one of the following; maximizing an amount of dose of the second category in the target volume and/or minimizing an amount of dose of the first category in the OAR.

According to another aspect a computer program product comprising computer-readable code means is provided which, when run in a computer, will cause the computer to perform the method of the present invention.

According to yet another aspect a computer system comprising a processor and a program memory is provided, the program memory holding a computer program product in such a way that it can be executed by the processor.

According to an additional aspect a radiation therapy treatment planning system is provided comprising a computer system as described above.

The concept of the invention may be applied to any radiation modality (photons, electrons, protons etc.) and treatment technique. For protons it builds on dividing the delivered dose per voxel into two portions or categories; one portion from energy deposition at low LET and one portion from energy deposition at high LET. The reason for dividing the dose distribution into doses of a first category ("Clean dose") and a second category ("Dirty dose") is that in radiotherapy with ions (protons and heavier ions), the RBE from a certain amount of delivered physical dose remains a difficult quantity to model. Current RBE models are inaccurate and this RBE model uncertainty is mainly a concern in or near OAR where a large fraction of the dose delivered is of the second category, i.e. "dirty". Typically, the high LET portions of a field are located at the distal edge per beam. Based on the divisions, it is possible to evaluate the plan quality, and in a further step to more effectively re-distribute the dose or LET portions inside the human body, thus making the plan more effective and accurate.

The two dose quantities can be used as input to a process for optimization or evaluation. For example, one can form the ratio of the high LET dose portion over the total dose per voxel. This ratio is a number between 0 and 1. In the OAR one can request this ratio to be below a certain threshold, say 10%. Similarly, in an optimization one can request this ratio to be maximized in the target volume.

It should be understood that the concept of "Dirty dose" and its applications described above is applicable beyond protons and LET. Collimators are used in radiation treatment to provide conformal shaping of the beam (photons, protons, electrons) to match the border of the target volume. One type of collimator widely used is the multileaf collimator (MLC) which comprises a number of metal collimator plates or "leaves" of a high atomic numbered material, usually tungsten, that can move independently in and out of the path of a beam in order to block it. The particles (photons, protons, electrons) in the penumbra of the beam pass close to or through the leaves which introduces uncertainties in the dose determination. Hence, one can treat dose from energy depositions where this occur as "Dirty dose". Another example concerns RBE models for protons and ions. These models are associated with large uncertainties. One can treat energy depositions (=dose) as "Dirty dose" if the RBE factor determination is inaccurate. If one evaluates the RBE factor for multiple models, a possible metric for this can be to evaluate how much RBE values from multiple models differs.

BRIEF DESCRIPTION OF THE DRAWINGS

These and other features, aspects and advantages of the present invention will be further explained in the following description with reference to the accompanying drawings, in which.

Herein, identical reference numerals are used, where possible, to designate identical elements that are common to the figures. Also, the images in the drawings are simplified for illustrative purposes and are not necessarily depicted to scale.

DETAILED DESCRIPTION

Figure 1:
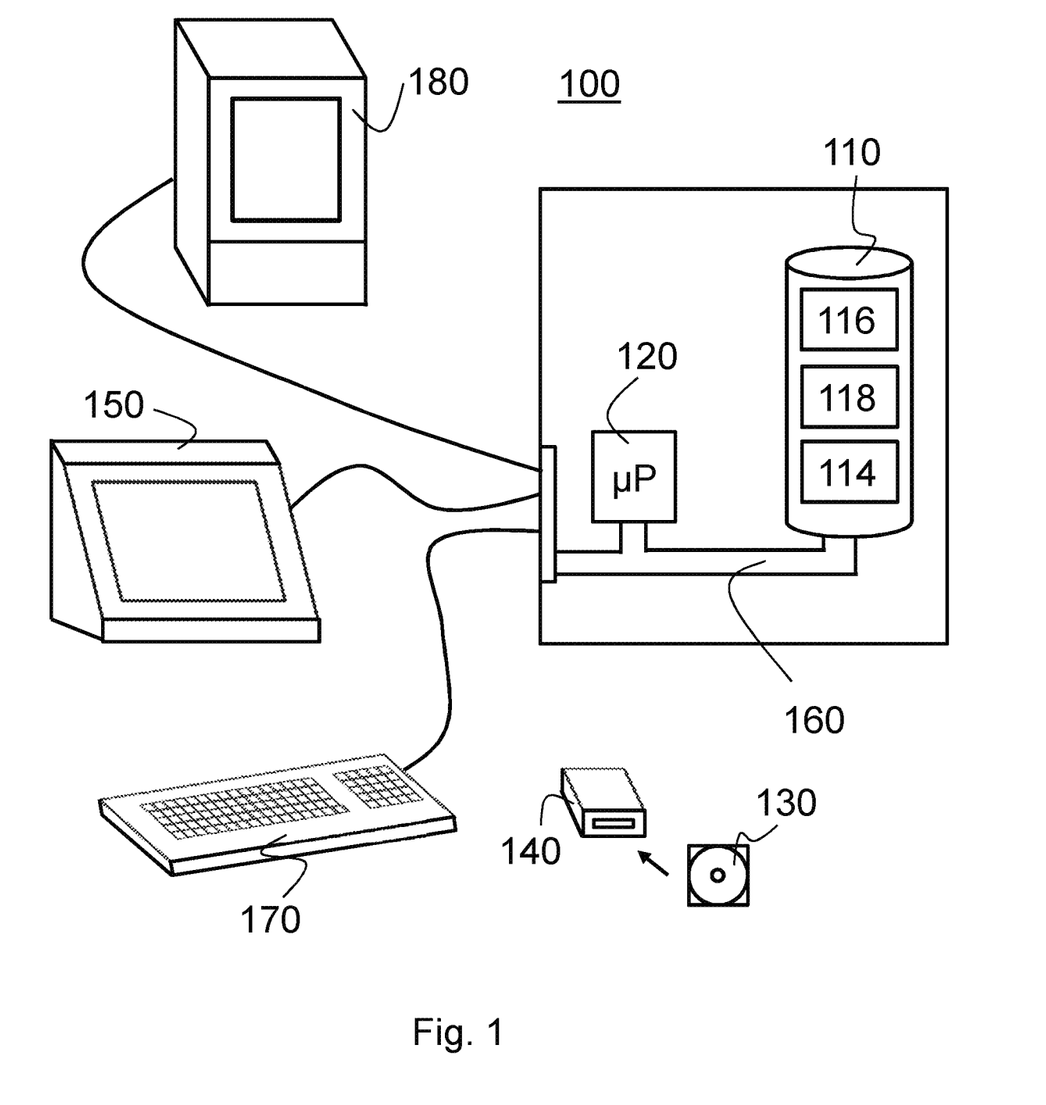
FIG. 1 schematically shows a computer-based system for evaluating, visualizing, generating and improving a radiation therapy treatment plan.

FIG. 1 shows a simplified schematic representation of a computer-based system 100 for generating a radiation therapy treatment plan 114, according to the present invention. The computer-based system 100 includes a memory or database 110 having a radiation therapy treatment plan 114 stored thereon, and a computer program 116 for generating an improved radiation therapy treatment plan 118. Memory 110 can be any volatile or non-volatile memory device such as a flash drive, hard drive, optical drive, dynamic random-access memory (DRAM), static random-access memory (SRAM), and any other suitable device for storing information and later information retrieval and use for data processing. Also, the system 100 includes one or more hardware processors 120 for performing data processing, which are able to access the memory 110. The hardware processor 120 can be made of one or more of a central processing unit (CPU), digital signal processor (DSP), reduced instruction set computer (RISC), application specific integrated circuit (ASIC), complex programmable logic device (CPLD), field-programmable gate arrays (FPGA), parallel processor systems, or a combination of these different hardware processor types.

The computer program 116 is made of computer-readable instructions that can be transferred to hardware processor 120 and can be executed by hardware processor 120. When executed on the hardware processor 120, the computer readable instructions will perform a method for generating an improved radiation therapy treatment plan 118. Results of the processing that is performed by the hardware processor 120 when executing the computer program 116 can be stored in memory 110, for example the improved radiation therapy treatment plan 118, and associated data. Hardware processor 120 can also access the memory 110 via direct memory access (DMA), and can also use a cache memory for storing temporary processing results. The computer program 116 can also be stored on a non-transitory computer readable medium 130, for example a universal serial bus (USB) flash drive, optical data carriers such as CD-ROM, DVD-ROM, and Blu-Ray disk, floppy disk, swappable hardware drives, USB external hard drive (HDD), or any other portable information storage device, so that the computer program 116 can be transferred to different computing systems, and also be loaded to the memory 110 of system 100. This can be done by connecting the computer readable medium 130 via a data reader/writer 140 to the system 100, for example an optical drive, USB interface, etc.

Moreover, the system 100 also includes a display unit 150 that has a display driver that allows visualization of results of the data processing, for example to visualize three-dimensional (3D) representations of a target volume of a patient containing, for example, a tumor or cancer cell, and healthy organs-at-risk for which dose delivery has to be prevented, 3D contour data, or two-dimensional (2D) slice representations for various intersection directions and for LET distribution in both the target volume and for organs-at-risk, etc. For example, a 3D computer reproduction of a CT scan can be displayed. Also, display unit 150 can display dose and LET volume histograms (DVH and LVH) that summarize 3D dose and LET distributions by using a graphical 2D format. For example, the display unit 150 is configured to show comparative DVH and LVH diagrams for volumes of the patient showing a dose contribution of the radiation therapy treatment plan 114, and for the same volumes of the optimized or improved radiation therapy treatment plan 118, so that also the LET distribution can be visually compared. Moreover, the LET representation can be visualized to form an LET map or any other visual representation of LET distribution. The display unit 150 can also display a 1D line profile of dose and LET and other quantities.

The display unit 150 is used for displaying a 3D scan of the patient that is made prior to the treatment, during the treatment or after the treatment. For example, a 3D computer reproduction of a CT scan can be displayed. Also, display unit 150 can display LET, dose and/or DVH that summarizes 3D dose distribution by using a graphical 2D format or using a numerical format. For example, the display unit 150 is configured to show comparative LET diagrams for volumes of the patient showing a cancer cell destruction or dose contribution of the radiation therapy treatment plan 114. This is shown and compared for the same volumes of the optimized or improved radiation therapy treatment plan, so that the improvement can be visually compared. Also, it is possible that the display unit 150 is equipped with a touch screen functionality and can display a graphical user interface to operate system 100.

In addition, computer system 100 has a system bus 160 that connects the hardware processor 120, memory 110, data reader 140, touch screen, and various other data input-output interfaces and peripheral devices that are not shown. For example, the computer system 100 can be connected to a keyboard 170 for data input by a user and may be connected to an external radiation therapy treatment planning device 180 that has created the radiation therapy treatment plan, for example a powerful special-purpose computer. Also, the system 100 may be connected to a CT scanner that is not shown. For example, external device 180 that created the radiation therapy treatment plan 114 may be able to develop a dose and LET distribution calculation algorithm that is coded into software, has access to radiation data on prescribed dose distribution, and machine calibration data, and patient-specific information on the target volume of and organs-at-risk of the patient. This external device 180 can then deliver the radiation therapy treatment plan 114 to computer system 100 for evaluation, visualization, creating a new plan, improving an existing plan taking the LET distribution into account. However, it is also possible that computer program 116 is run on the external device itself, thereby not only generating the radiation therapy treatment plan 114, but also generating the improved radiation therapy treatment plan 118.

Figure 2:
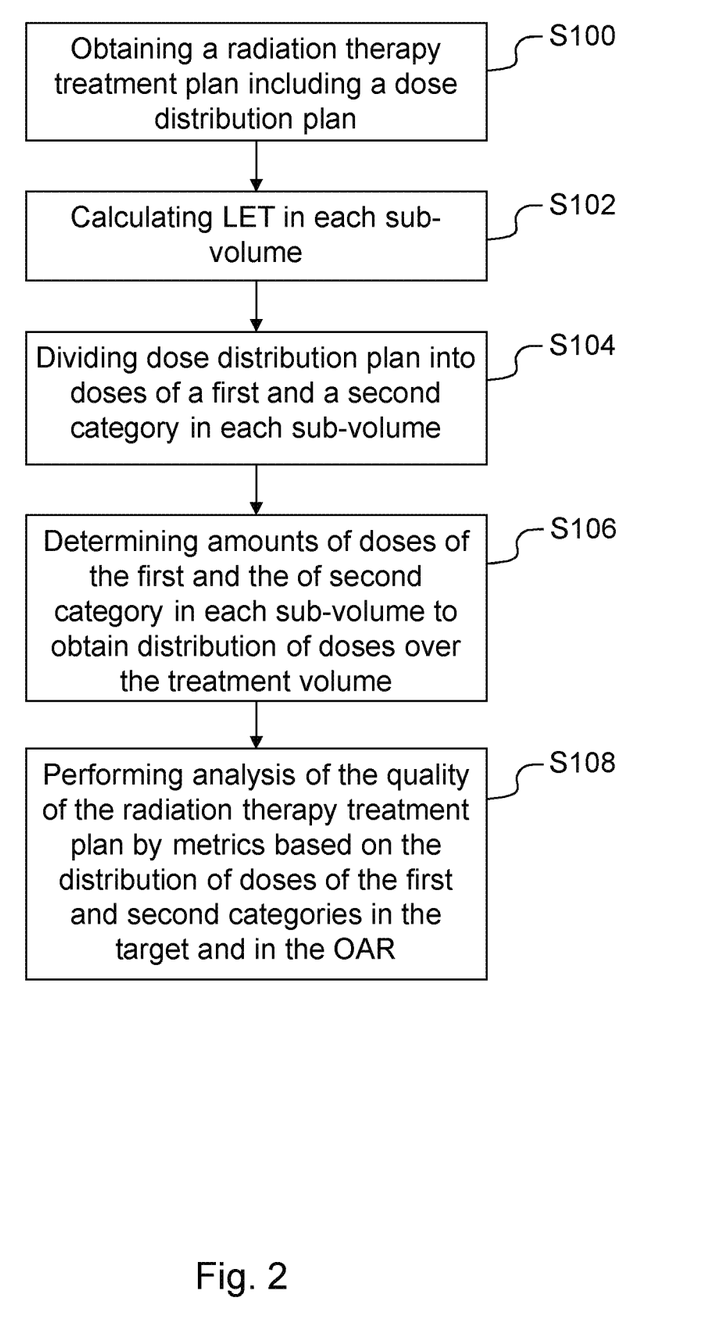
FIG. 2 shows a flow chart representing the steps of a computer-based method for evaluating a radiation therapy treatment plan.

Turning now to FIG. 2, the computer-based method will be closer described. As mentioned above the method is used to evaluate a radiation therapy treatment plan used in a radiation therapy apparatus for a treatment volume of a body having a target volume and one or more organs at risk (OAR), the treatment volume comprising a plurality of sub-volumes. In step S100 a radiation therapy treatment plan is obtained for the treatment volume. The radiation therapy treatment plan 114 has a dose distribution, which previously has been created for radiation treatment with the radiation therapy apparatus.

In context of the present invention it should be understood that there are several types of radiation therapy treatment plans for external radiation treatment. These treatment plans can include but are not limited to conformal radiotherapy, intensity modulated radiation therapy (IMRT) like for example pencil beam scanning (PBS) therapy, image guided radiation therapy (IGRT), 4-dimensional radiation therapy (4D-RT), stereotactic radiotherapy and radiosurgery, proton therapy, carbon ion therapy, electron beam radiotherapy or adaptive radiotherapy. For example, in order to generate an IMRT treatment plan, the specialist needs to identify the region to be treated in the patient's body and assess the OAR using conventional scanning techniques like computer tomography (CT). The target volume is usually an organ in a patient's body that is affected by a tumor, for example a cancer.

In step S102 a linear energy transfer, LET, distribution is calculated for each of the sub-volumes of the treatment volume. The LET distribution may be obtained from the radiation therapy treatment plan 114. Alternatively, the computer program 116 stored in the memory 116 is configured to make LET distribution calculations in the target volume or OAR and calculate the relationships between the dose and the LET portions in the initial radiation therapy treatment plan. It should be understood that when describing the LET distribution it may be the distribution of track-averaged LET, dose-averaged LET, or the like.

In step S104 the dose distribution for the treatment plan in each sub-volume is divided into doses of a first category and a second category, wherein the first dose category is associated with an energy deposition below a first LET threshold and the second dose category comprises doses with an energy deposition above a second LET threshold. The first category may constitute low LET regions and the second category may constitute high LET regions. The threshold for high LET regions may be above 3 kiloelectronvolts per micrometer (keV/μm) if specified in absolute numbers.

The first and second LET threshold may be the same or they may be different. In one embodiment the first and second threshold are selectable by a user of the radiation therapy apparatus.

In step S106 an amount of dose of the second category in each sub-volume is determined. The amount of dose of the second category may be determined in different ways. For example, the amount of dose of the second category in each sub-volume, or voxel, may be determined in absolute numbers as an absorbed dose, or as a fraction of the amount of dose of the second category in relation to the total dose per sub-volume. For example, the fraction of doses of the second category may be 10% of the total dose.

In step S108, an analysis of the quality of the radiation therapy treatment plan is performed by metrics based on the obtained distribution of doses of the first and of the second category in the target volume and in the OAR. The analysis is based on, but is not limited to, assessing the distribution of "Dirty dose" in the OAR and in the target volume. For this purpose, the same dose metrics used for the total dose can be used such as dose volume histograms, dose uniformity index etc. The plan can also be analysed with respect to robustness of total dose and "Dirty dose".

Figure 3:
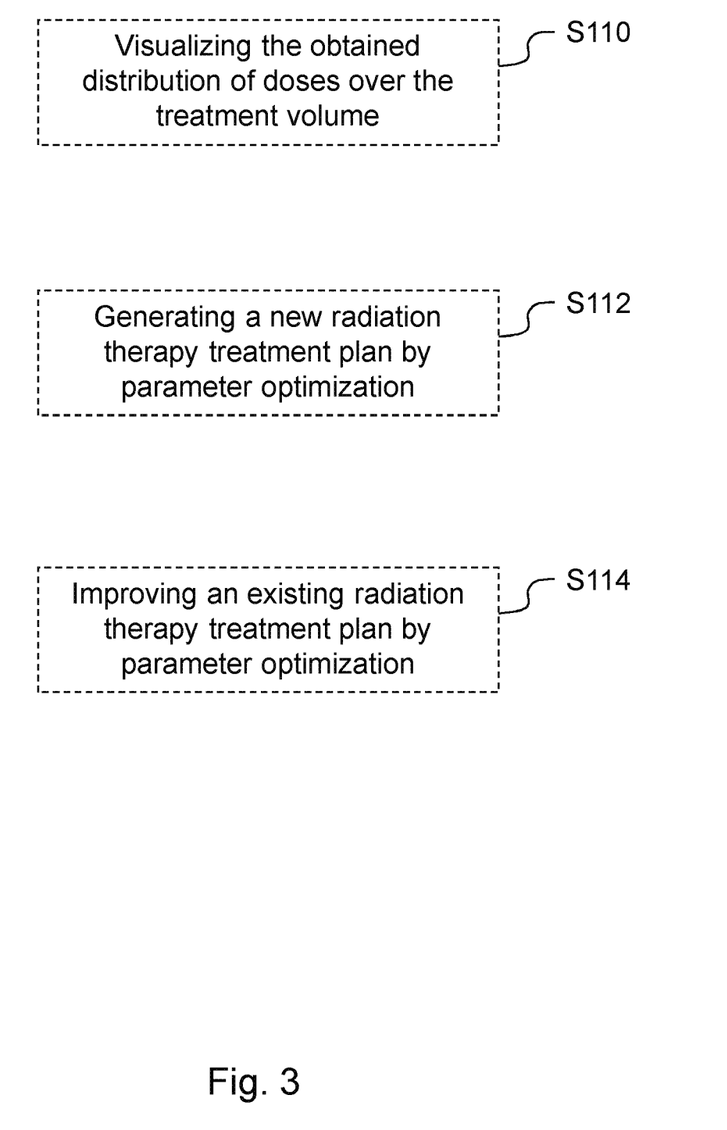
FIG. 3 shows additional steps of a computer-based method for visualizing, generating and improving a radiation therapy treatment plan.

Turning now to FIG. 3, additional steps of the computer-based method, representing alternative embodiments, are outlined. In a first embodiment comprising an optional step S110, the obtained distribution of doses of the first and of the second category over the treatment volume is visualized, such that regions with excessive concentrations of doses of the first and of the second category are assessable. This provides a visual aid for the medical practitioner to identify the regions e.g. with high concentrations of "dirty dose".

In yet another embodiment, the step of visualizing comprises visualizing the total dose and LET distributions together with the obtained distribution of doses of the first and of the second category over the treatment volume, wherein the amount of dose of the second category in each sub-volume is specified as a fraction of the amount of dose of the second category in relation to the total dose per sub-volume, such that regions with combined excess of high LET concentration and excessive concentration of first or second dose category are assessable.

In optional step S112, parameter optimization is performed for a set of parameters of the radiation therapy apparatus with the purpose of generating a new radiation therapy treatment plan. In this embodiment, the radiation therapy treatment plan obtained in step S100 may be a generic plan based e.g. on standard, estimated values adapted to the treatment volume, target volume and OAR, for instance obtained from a database. The parameter optimization is based on the radiation therapy treatment plan for the treatment volume and the amount of dose of the second category in each sub-volume and is performed by the computer or microprocessor 120. When the parameter optimization is performed, one objective is that the amount of dose of the second category in the target volume is as high as possible or at least above a threshold. while the amount of dose of the second category, i.e. the "dirty dose", is reduced in the OAR. This is accomplished e.g. by simulating a variation of the set of parameters of the radiation therapy apparatus and calculating a direct relationship between the variation of the set of parameters and the variation of the amount of dose of the second category in the OAR, thereby generating an improved radiation therapy treatment plan.

In an alternative embodiment, the radiation therapy treatment plan may be an existing radiation therapy treatment plan 114 accessed from the memory 110 in the computer 120 or from any other media 130 or device 180 as explained above. The radiation therapy treatment plan 114 is used as a reference plan, serving as a base when generating the improved treatment plan 118.

In optional step S114, based on an existing plan 114, parameter optimization is performed for a set of parameters of the radiation therapy apparatus with a computer using the amount of doses of the second category in each sub-volume, such that the amount of dose of the second category is below a first threshold in the OAR, and above a second threshold in the target volume, while at least preserving the plan quality of the existing radiation therapy treatment plan 114, thereby generating an improved radiation therapy treatment plan 118.

This parameter re-optimization may be performed to minimize "Dirty dose" in OAR and maximize "Dirty dose" in target volume while preserving the initial plan quality with respect to dose distribution quality and other qualities. It may comprise:
- verifying that a dose of the sub-volumes in OAR regions is not higher than the initial or reference dose at the sub-volumes in the initial radiation therapy treatment plan;
- verifying that a dose at sub-volumes in the target volume region is not lower than the reference dose at the sub-volumes of the initial radiation therapy treatment plan or is not lower than the prescribed dose to the target volume;
- verifying that LET at individual sub-volumes in OAR regions is not higher than the initial LET at the sub-volumes of the initial radiation therapy treatment plan; and/or
- verifying that LET at individual sub-volumes of the target volume region is not lower than the initial LET at the sub-volumes of the initial radiation therapy treatment plan.

The user of the machine chooses a degree of optimization during the radiation therapy treatment planning process. In alternative embodiments, machine learning algorithms can be deployed, which allow to account for individualistic characteristics of the patient undergoing the treatment.

With an increasing LET the damage becomes more severe and more difficult to repair by the cells irradiated with charged particles resulting in higher radiation lethality, which is reflected by a higher RBE. However, there is an LET maximum after which the effectiveness is reduced and RBE decreases. Thus, it is therefore possible to optimize the distribution of the high LET portions by minimizing the high LET portions from the regions where high LET energy depositions are not desired such as in OARs, or vice-versa, maximizing the high LET portions in the target volume.

In order to re-distribute the high LET portions and low LET portions, the computer program 116 divides the LET in the first and second category as described previously. The computer program 116 quantifies the information on a per voxel or sub-volume basis since the most effective re-distribution can be achieved on a micro-scale basis and the most commonly micro-scale volume quantity are voxels. The program takes the average of the LET portions contained in the voxels. The distribution could create an LET map, LET visualization or any other suitable algorithm. If there is a high average LET value, this will indicate that the RBE factor computed in this voxel may be inaccurate and the program will try to account for this uncertainty by adjusting the LET values by re-distributing the LET values for example by penalizing high "Dirty dose" in the OAR regions. This will create a further optimized radiation therapy treatment plan.

Figure 4:
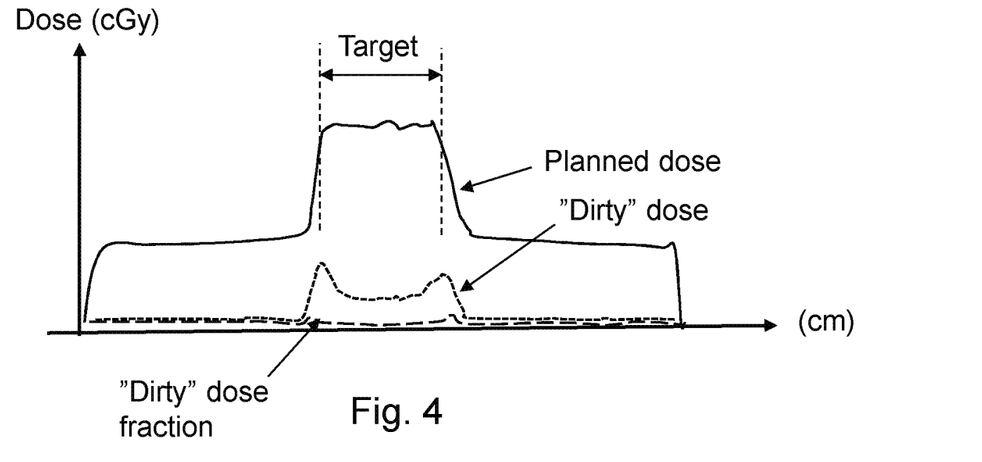
FIG. 4 shows a graph of planned dose, "Dirty dose" and "Dirty dose" fraction along a radiation distance where the target volume is placed in the center.

FIG. 4 shows a graph of planned dose, "Dirty dose", i.e. the second category with an energy deposition above the second LET threshold, and "Dirty dose" fraction measured in cGy along a radiation distance where the target volume is placed in the center. As is obtainable in FIG. 3, the planned dose is highest in the central target volume region. If there is a high amount of dose of the second category in one sub-volume, this indicates that the RBE factor that is computed in this sub-volume may be inaccurate or at least have a high degree of uncertainty. By performing parameter optimization, it is possible to redistribute the second category ("Dirty dose") away from the OAR while preserving the amount of dose of the second category in the target volume. The second category may be specified in terms of an absolute number, i.e. as the absorbed dose in grays (Gy) or as a fraction of the amount of dose of the second category in relation to the total dose per sub-volume, such as for instance 0.1 or 10%.

Furthermore, a computer program product is introduced for performing parameter optimization. The computer program product 130 comprises computer-readable code means, which when run in the computer carries out the method described above.

The following abbreviations are used:
CT computer tomography
CTV clinical tumor volume
DICOM digital imaging and communications in medicine
DVH dose volume histogram
EHR electronic health record system
eMIX electronic medical information exchange system
GUI graphical user interface
GTV gross tumor volume
HIS hospital information system
HIM health information management system
IMRT intensity modulated radiation therapy
LET linear energy transfer
LVH LET volume histogram
MLC multileaf collimator
Mill magnetic resonance imaging system
MU monitor units
OAR organ at risk
PBS pencil beam scanning
PET positron emission tomography
PTV planning tumor volume
QA quality assurance
QC quality control
US ultrasonography
RBE relative biological effectiveness
ROI region of interest
RVS record and verify system SPECT single photon positron emission tomography

The invention claimed is:

1. A computer-based method of evaluating a radiation therapy treatment plan arranged to be used in a radiation therapy apparatus for a treatment volume of a body having a target volume and one or more organs at risk, OAR, the treatment volume comprising a plurality of sub-volumes, wherein the method comprises:
   obtaining a radiation therapy treatment plan for the treatment volume, the radiation therapy treatment plan comprising a dose distribution for radiation treatment with the radiation therapy apparatus for the treatment volume of the body having the target volume and the OAR;
   calculating a linear energy transfer, LET, in each sub-volume based on the dose distribution to obtain an LET distribution over the treatment volume;
   dividing the dose distribution into a first dose distribution of a first category and a second dose distribution of a second category in each sub-volume, wherein the first dose distribution of the first category comprises an amount of dose arising from energy deposition with an LET below a first LET threshold and the second dose distribution of the second category comprises an amount of dose arising from energy deposition with an LET above a second LET threshold; and
   performing an analysis of the quality of the radiation therapy treatment plan by metrics based on the first dose distribution of the first category and the second dose distribution of the second category in the target volume and in the OAR.

2. The method according to claim 1, wherein the amount of dose of the second category in each sub-volume is specified in absolute numbers as absorbed dose.

3. The method according to claim 1, wherein the amount of dose of the second category in each sub-volume is specified as a fraction of the amount of dose of the second category in relation to a total dose distribution per sub-volume.

4. The method according to claim 1, wherein the first and second LET thresholds are the same.

5. The method according to claim 1, wherein the first and second LET thresholds are different.

6. The method according to claim 1, wherein one or more additional LET thresholds are used to subdivide the doses of at least one of the first category or the second category into subcategories comprising doses with energy depositions with an LET below or above the one or more additional LET thresholds.

7. The method according to claim 1, wherein the LET thresholds are selectable by a user of the radiation therapy apparatus.

8. The method according to claim 1, further comprising:
   visualizing the first dose distribution of the first category and the second dose distribution of the second category over the treatment volume, such that regions with excessive concentrations of the first category and of the second category are assessable.

9. The method according to claim 8, wherein the step of visualizing comprises visualizing a total dose distribution per sub-volume and LET distributions together with the first dose distribution of the first category and the second dose distribution of the second category over the treatment volume, wherein the amount of dose of the second category in each sub-volume is specified as a fraction of the amount of dose of the second category in relation to the total dose distribution per sub-volume, such that regions with combined excess of high LET concentration and excessive concentration of the first category or the second category are assessable.

10. The method according to claim 1, wherein the step of obtaining a radiation therapy treatment plan comprises obtaining an initial, estimated radiation therapy treatment plan, the method further comprising:
    generating a new radiation therapy treatment plan for the treatment volume by performing a parameter optimization for a set of parameters of the radiation therapy apparatus with a computer using the amount of dose of the second category in each sub-volume, such that the amount of dose of the second category is below a first threshold in the OAR, and above a second threshold in the target volume.

11. The method according to claim 10, wherein said parameter optimization includes at least one of the following:
    maximizing the amount of dose of the second category in the target volume; or
    minimizing the amount of dose of the first category in the OAR.

12. The method according to claim 1, wherein the step of obtaining a radiation therapy treatment plan comprises obtaining an existing radiation therapy treatment plan for the treatment volume, the method further comprising:
    adjusting the existing radiation therapy treatment plan for the treatment volume by performing a parameter optimization for a set of parameters of the radiation therapy apparatus with a computer using the amount of dose of the second category in each sub-volume, such that the amount of dose of the second category is below a first threshold in the OAR, and above a second threshold in the target volume, while at least preserving the plan quality of the existing radiation therapy treatment plan, thereby generating an improved radiation therapy treatment plan.

13. A computer program product comprising non-transitory computer-readable code means which, when run in a computer, will cause the computer to perform the method according to claim 1.

14. A computer system comprising a processor and a program memory, the program memory holding the computer program product according to claim 13 in such a way that it can be executed by the processor.

15. A radiation therapy treatment planning system comprising the computer system according to claim 14.

* * * * *